United States Patent
Chang et al.

(10) Patent No.: US 9,778,151 B2
(45) Date of Patent: Oct. 3, 2017

(54) SAMPLE COLLECTION DEVICE AND SAMPLE COLLECTION DEVICE ARRAY

(71) Applicant: BIO MATERIALS ANALYSIS TECHNOLOGY INC., Hsinchu County (TW)

(72) Inventors: Pin Chang, Hsinchu (TW); Hung-Jen Chen, Hsinchu (TW)

(73) Assignee: BIO MATERIALS ANALYSIS TECHNOLOGY INC., Hsinchu County (JP)

(*) Notice: Subject to any disclaimer, the term of this patent is extended or adjusted under 35 U.S.C. 154(b) by 0 days.

(21) Appl. No.: 15/073,667

(22) Filed: Mar. 18, 2016

(65) Prior Publication Data

US 2016/0377513 A1 Dec. 29, 2016

(30) Foreign Application Priority Data

Jun. 26, 2015 (TW) .............................. 104120757 A

(51) Int. Cl.
| | |
|---|---|
| *G01N 1/28* | (2006.01) |
| *H01J 37/20* | (2006.01) |
| *H01J 37/26* | (2006.01) |
| *H01J 37/32* | (2006.01) |

(52) U.S. Cl.
CPC ............ *G01N 1/2813* (2013.01); *H01J 37/20* (2013.01); *H01J 37/26* (2013.01); *H01J 37/32009* (2013.01)

(58) Field of Classification Search
CPC .. H01J 37/20; H01J 37/26; H01J 37/16; H01J 37/222; H01J 37/261; B01L 3/508; G01N 1/28; G01N 1/4022; G01N 23/02

USPC .......... 250/440.11, 307, 304, 306, 310, 311, 250/422.11
See application file for complete search history.

(56) References Cited

U.S. PATENT DOCUMENTS

| | | | | |
|---|---|---|---|---|
| 5,406,087 | A * | 4/1995 | Fujiyoshi ................ | B01L 3/508 250/440.11 |
| 6,992,026 | B2 | 1/2006 | Fukuyo et al. | |
| 7,807,979 | B2 * | 10/2010 | Liu .......................... | H01J 37/20 250/306 |
| 8,969,827 | B2 * | 3/2015 | Hsieh ...................... | B01L 3/508 250/304 |
| 9,384,942 | B2 * | 7/2016 | Hsieh ...................... | B01L 3/508 |
| 2010/0193398 | A1 * | 8/2010 | Marsh .................... | G02B 21/34 206/710 |
| 2014/0007709 | A1 | 1/2014 | Hsieh et al. | |

(Continued)

FOREIGN PATENT DOCUMENTS

TW I330380 9/2010

*Primary Examiner* — David A Vanore
(74) *Attorney, Agent, or Firm* — Jianq Chyun IP Office

(57) ABSTRACT

A sample collective device includes two substrates and a spacer. Each substrate has a first surface and a second surface, and the two substrates are arranged with the first surfaces facing each other. The spacer is disposed between the two first surfaces for bonding and fixing the two substrates and forming a sample containing space. In addition, each of the substrates includes a first weakening structure located in the periphery of the sample containing space and exposed on the first surface. A sample collective device array including a plurality of the aforementioned sample collective devices is also provided.

31 Claims, 10 Drawing Sheets

(56) References Cited

U.S. PATENT DOCUMENTS

2014/0042318 A1\* 2/2014 Yaguchi .................. H01J 37/20
250/311

\* cited by examiner

SAMPLE COLLECTION DEVICE AND SAMPLE COLLECTION DEVICE ARRAY

CROSS-REFERENCE TO RELATED APPLICATION

This application claims the priority benefit of Taiwan application serial no. 104120757, filed on Jun. 26, 2015. The entirety of the above-mentioned patent application is hereby incorporated by reference herein and made a part of this specification.

BACKGROUND

Technical Field

The present disclosure relates to a sample collection device, and relates particularly to a sample collection device adapted for observation by a microscope.

Description of Related Art

Along with developments in microscopic observation technology, various types of microscopes, for example, an optical microscope, an atomic force microscope (AFM), a transmission electron microscope (TEM), a scanning electron microscope (SEM) and the like have been developed in response. In addition, different types of microscopes require different sample specimens, for example, a liquid sample specimen, a dry sample specimen and such.

However, when a liquid sample specimen containing suspended particles is prepared into a dry sample specimen using conventional techniques, an external force received by the suspended particles will be non-uniform because the liquid sample specimen is affected by surface tension, which causes the suspended particles to drift and converge during the drying process such that a polymerized group forms after drying. This converging phenomenon affects the interpreted results when the microscope is used to observe the dried sample specimen.

In addition, US patent publication number US 2014/0007709 A1 discloses a dried liquid sample specimen device and method, however the dried liquid sample specimen device disclosed includes upper and lower two substrates, wherein the two substrates cannot be easily opened, such that the observation instrument is unable to approach the surface of the substrate at a close distance. Therefore, the aforementioned dried liquid sample specimen device may be applicable only to particular microscopes, for example, an electron microscope. However, an atomic force microscope for example, requires a probe head to approach the dry sample specimen at a close distance, to a distance in the nanometer range, such that this dried liquid sample specimen device cannot be used.

SUMMARY

The present disclosure provides a sample collective device, which may effectively prevent aggregation phenomenon caused by surface tension of a liquid to provide a uniform dried sample specimen.

The present disclosure provides an easily openable sample collective device, which may expose a dried sample on the specimen surface to provide a bare dried sample specimen, therefore significantly increasing suitable range of the specimen for observation analysis.

The sample collective device of the present disclosure includes two substrates and a spacer. Each of the substrates has a first surface and a second surface, and the two first surfaces are disposed facing each other. The spacer is disposed between the two first surfaces, and used for bonding and fixing the two substrates to form a sample containing space between the two substrates. In addition, each of the substrates has a first weakening structure, and the first weakening structure is located at a periphery of the sample containing space and exposed on the first surface.

The present disclosure provides a sample collective device array which may be separated into a plurality of the aforementioned sample collective devices.

The sample collective device array of the present disclosure includes a plurality of the aforementioned sample collective devices, wherein the sample collective devices are arranged in an array and connected together, and are defined by a plurality of cutting paths. In other words, after cutting the sample collective device array along the cutting path, the plurality of sample collective devices separated from each other may be obtained.

The present disclosure further provides a manufacturing method of a sample collective device. First an insulating layer is formed on a first surface and a second surface of a semiconductor substrate which are opposite each other. Next, the insulating layer located at a periphery of the first surface is removed, and a bonding layer is formed on the exposed first surface. Then, the insulating layer is patterned on the first surface and the second surface, wherein the insulating layer on the first surface exposes a part of the first surface, and the insulating layer on the second surface exposes a part of the second surface. Then, a first weakening structure is formed on the part of the first surface exposed by the insulating layer. The aforementioned steps are repeated on another semiconductor substrate. Then, the two semiconductor substrates are bonded together by the bonding layer of each, wherein the two bonding layers form a spacer which is used to connect and fix the two semiconductor substrates, and a sample containing space is formed between the two semiconductor substrates and the spacer.

The two substrates of the sample collective device of the present disclosure is fixed by a spacer, so as to provide a suitable height between the two substrates, to allow a liquid sample to be absorbed into kept in a sample containing space through, for example, by the capillary phenomenon and such, and maintain the liquid sample in a uniform thickness. In this way, the flowing of the liquid during the drying process may be suppressed to prevent the aggregation phenomenon of the suspended particles, such that the suspended particles may maintain their original distribution and characteristics during the drying process. Besides, in the present disclosure, a weakening structure is formed corresponding to a periphery of the sample containing space, and corresponding to a location other than the spacer. Particularly, a first weakening structure exposed on a first surface of a substrate may be used to separate different parts of the substrates on two sides of the weakening structure by applying a force to the weakening structure after the liquid sample is dried. The sample collective device can then be opened and the exposed sample specimen is formed. The dried sample specimen has a broad range of applicability, and is suitable for various types of microscope observation techniques. In addition to an electron microscope, it may be suitable for, for example, analysis methods such as an atomic force microscope, MALDI-TOF-MS, or even contact probes for electrical testing.

Several exemplary embodiments accompanied with figures are described in detail below to further describe the disclosure in details.

BRIEF DESCRIPTION OF THE DRAWINGS

The accompanying drawings are included to provide a further understanding of the present disclosure, and are incorporated in and constitute a part of this specification. The drawings illustrate embodiments of the present disclosure and, together with the description, serve to explain the principles of the present disclosure.

DESCRIPTION OF THE EMBODIMENTS

Figure 1A:
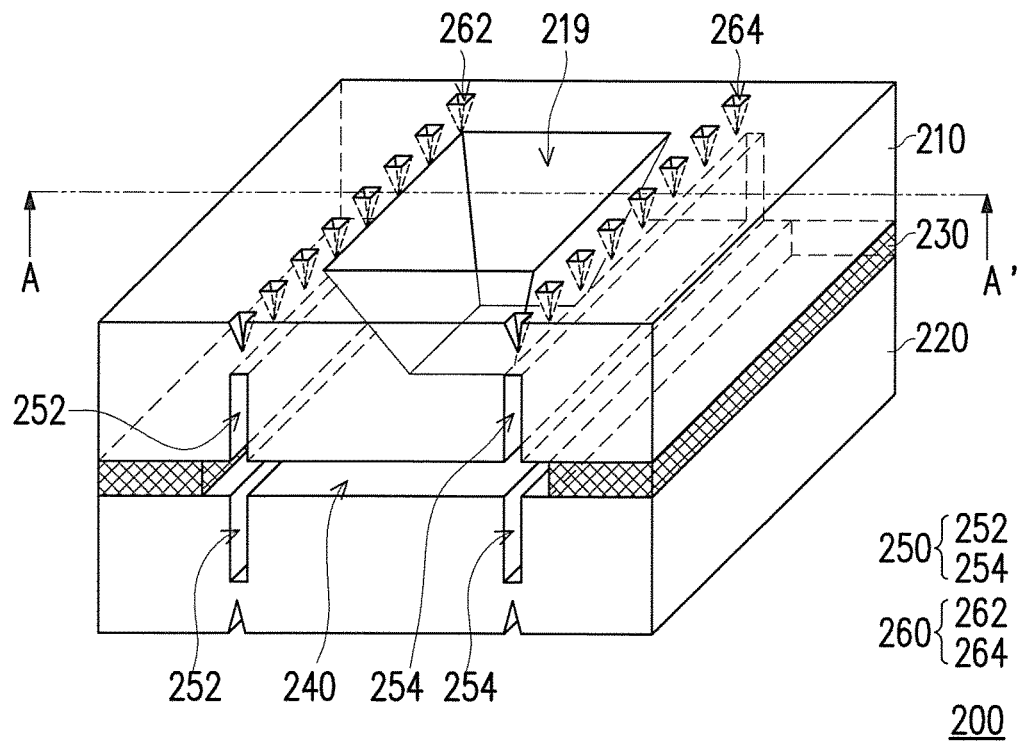
FIG. 1A is a three-dimensional diagram of a sample collection device according to an embodiment of the present disclosure.

Reference will now be made in detail to the present preferred embodiments of the present disclosure, examples of which are illustrated in the accompanying drawings. Wherever possible, the same reference numbers are used in the drawings and the description to refer to the same or like parts.

Figure 1B:
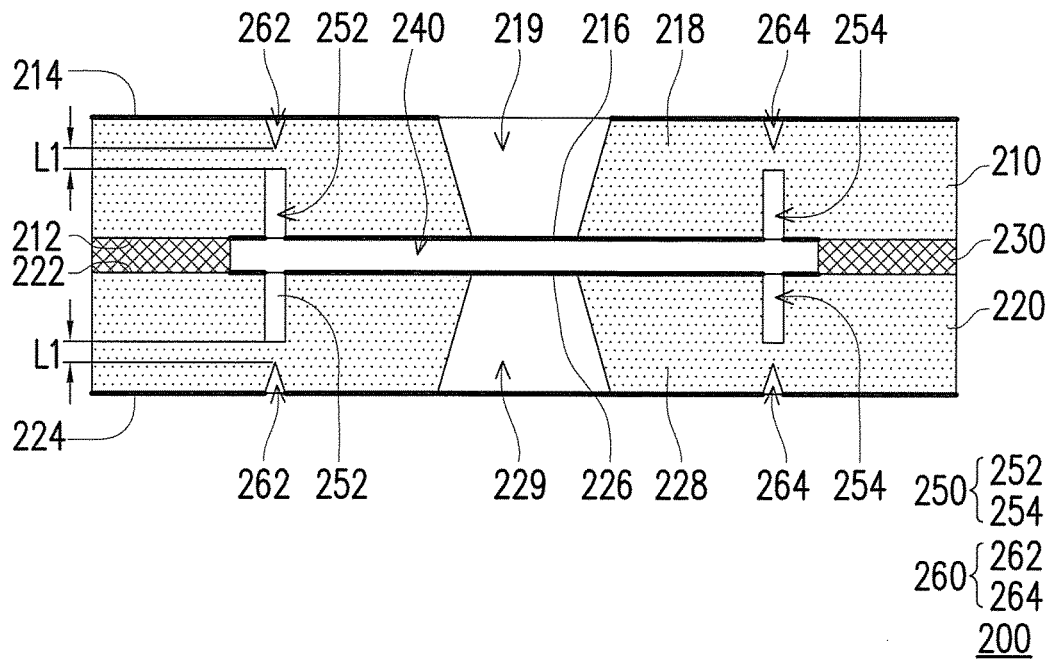
FIG. 1B is a cross-sectional diagram of the sample collection device of FIG. 1A along the surface A-A'.

FIG. 1A is a three-dimensional diagram of a sample collection device according to an embodiment of the present disclosure. FIG. 1B is a cross-sectional diagram of the sample collection device 200 of FIG. 1A along the surface A-A'. The sample collective device 200 of the present embodiment includes two substrates 210, 220 and a spacer 230, wherein the substrate 210 has a first surface 212 and a second surface 214, the substrate 220 has a first surface 222 and a second surface 224, and the first surface 212 of the substrate 210 and the first surface 222 of the substrate 220 are arranged facing each other. The spacer 230 is disposed between the first surfaces 212 and 222, and is used for bonding and fixing the substrates 210 and 220 such that a sample containing space 240 is formed between the substrates 210 and 220. Here, the sample containing space 240 which is defined by the spacer 230, for example, is a flow path having two end-openings at a front and a rear. A liquid sample may pass through the two end-openings at the front and the rear and enter the sample containing space 240, and be held in the sample containing space 240.

In the present embodiment, the substrate 210 has a thin film 216 and a bottom 218 and the substrate 220 has a thin film 226 and a bottom 228. The thin films 216 and 226 are deposited on the bottoms 218 and 228 respectively, and the surfaces of the thin films 216 and 226 are namely the first surfaces 212 and 222, and are used to maintain the sample containing space 240. In the present embodiment, a method used for forming the thin films 216 and 226 at the bottoms 218 and 228 includes chemical vapor deposition, acid washing, surface material deposition, polymer deposition and the like, wherein the chemical vapor deposition method, for example, is by plasma enhanced chemical vapor deposition (PECVD). Regarding the manufacturing method, reference may be made to existing semiconductor manufacturing processes or micro-electromechanical manufacturing technologies and will not be repeated here.

A material of the thin films 216 and 226 may be silicon, silicon nitride, silicon oxide, silica, nitrogen silicon oxide, carbon, diamond film, graphene, silicon carbide, alumina, titanium nitride, titanium oxide, carbon nitride or a combination from the group above. In addition, if considering observation requirements that are applicable to the transmission electron microscope (TEM), the thin films 216 and 226 need to allow the electron beam of the transmission electron microscope to penetrate. Therefore, a material having a high electron penetration rate may be selected. In addition, a thickness of the thin films 216 and 226 may be altered according to design and actual requirements. For example, the thickness of the thin films 216 and 226 of the present embodiment are approximately 2 nanometers to 200 nanometers to facilitate observation by the transmission electron microscope. The aforementioned is an example of a silicon wafer manufacturing process, however, the present disclosure may also be applicable to other substrate materials but consideration must be given to the mechanical strength, density, transparency, electron penetration rate, integration of the manufacturing process of the thin film and substrate, residual stress and surface characteristics of the thin film.

Continuing, the thin films 216 and 226 of the present embodiment are used to provide the first surfaces 212 and 222 in contact with the liquid sample, and may be a hydrophilic material or a water repellent material. If hydrophilic material is selected, then the adsorption strength for absorbing a polar liquid sample is increased. If water repellent material is selected, then the adsorption strength for absorbing a non-polar liquid sample is increased. The surface characteristics of the thin films 216 and 226 may be adjusted through physical modification, for example, UV ozone modification, plasma modification or chemical modifications such as acid washing, etching, anodizing, connecting functional group and the like methods.

A material of the bottoms 218 and 228, for example, is a semiconductor material or a metal oxide material. The semiconductor material, for example, is a double polished or single polished single crystal silicon. The metal oxide material, for example, is aluminum oxide. A thickness of the bottoms 218 and 228 may also be altered according to the design or actual requirements, for example, if applicable to the transmission electron microscope, then it may be designed to approximately 0.2-0.8 millimeters.

The spacer 230 of the present embodiment has functions both to maintain the spacing between the two substrates 210 and 220 and to bond and fix the two substrates 210 and 220. A height of the spacer 230 is designed to a height sufficient to generate an absorption force similar to a capillary phenomenon. In the present embodiment, the height of the spacer 230 is between approximately 0.1 microns to 20 microns, and more preferably between 0.1 microns to 10 microns. In other words, the spacing between the two substrates 210 and 220, namely the height of the sample containing space 240, is between approximately 0.1 microns to 20 microns; and more preferably between 0.1 microns to 10 microns. An advantage thereof is: in addition to separating suspended particles larger than 10 microns in a portion of the liquid sample from the sample containing space 240, for example, it may also be applicable for separate observations of blood cells and the blood plasma in the blood.

Considering the material, manufacturing process or other possible factors of the substrates 210 and 220, the spacer 230 may be an adhesive material, for example, epoxy resin, UV glue or silicon material. Or, the spacer 230 may be a non-adhesive material, for example, silicon oxide, silicon and the like and for example bonds and fixes the substrates 210 and 220 by the anodic bonding between the silicon and the silicon oxide. The spacer 230 may use, for example, screen printing and sealant and the like coating methods to form the first surfaces 212 and 222 of the substrates 210 and 220. Or, the spacer 230 may be formed on the first surfaces 212 and 222 of the substrates 210 and 220 by chemical vapor deposition.

On the other hand, in the present embodiment, a first weakening structure 250 is formed on the first surface 212 of the substrate 210 and the first surface 222 of the substrate 220 respectively, wherein the first weakening structure 250 is located at the periphery of the sample containing space 240. The second surface 214 of the substrate 210 and the second surface 224 of the substrate 220 may also have a corresponding second weakening structure 260. The first weakening structure 250 and the second weakening structure 260 referred to here are structures with structural strengths lower than other parts of the substrates 210 and 220. In actuality, depressions may be formed by removing a part of the substrates 210 and 220, or implemented by performing modifications to partial regions of the substrates 210 and 220. Possible configurations for the first weakening structure 250 or the second weakening structure 260, for example, include two corresponding strip shaped structures located at two opposite sides of the sample containing space 240 or a plurality of opposing block shaped structures on two corresponding strip shaped paths.

In the present embodiment, the first weakening structure 250 includes two strip shaped depressions 252 and 254 located at two opposite sides of the sample containing space 240. In addition, the second weakening structure 260 includes a plurality of block shaped depressions 262 and 264 distributed on the path of the two strip shapes. Of course, possible configurations for the first weakening structure 250 and the second weakening structure 260 are not limited hereto. For example, the first weakening structure 250 also may also be formed by a plurality of block shaped depressions and the second weakening structure 260 may be two strip shaped depressions. Or, the first weakening structure 250 and the second weakening structure 260 may be any design which has a structure weakening effect, and will not be repeated here.

The substrates 210 and 220 of the present embodiment further includes observation windows 219 and 229 respectively, wherein the observation windows 219 and 229 are located on the second surfaces 214 and 224 respectively and corresponds with the sample containing space 240, and exposes a portion of the thin films 216 and 226 respectively.

More specifically, a base area of the observation windows 219 and 229 are approximately 1 square microns to 1 square millimeter. In the present embodiment, a photolithography and etching manufacturing processes may be performed to the bottoms 218 and 228 on the second surface 214 of the substrate 210 and the second surface 224 of the substrate 220, to obtain the observation windows 219 and 229.

A manufacturing method of a sample collective device of the present disclosure is enumerated below. FIGS. 2A-2E illustrate a manufacturing process of a sample collection device sequentially.

Figure 2A:
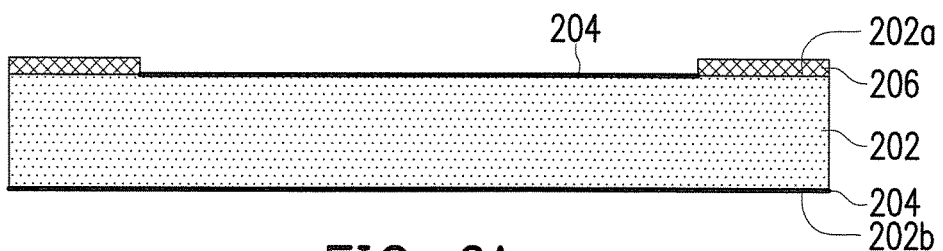
FIGS. 2A-2E illustrate a manufacturing process of a sample collection device sequentially.

First, as shown in FIG. 2A, a semiconductor substrate 202, for example, a silicon substrate is provided; and an insulating layer 204 is formed on a first surface 202a and a second surface 202b of the semiconductor substrate 202 respectively. Here, for example, chemical vapor deposition is performed to form a silicon nitride layer with a thickness of approximately 100 nanometers. The insulating layer 204 at the periphery of the first surface 202a is removed to expose a part of the first surface 202a; and a bonding layer 206 is formed at the exposed first surface 202a, for example, by deposition or oxidation and such method. Here, the bonding layer 206, for example, is a silicon oxide layer with a thickness of approximately 300-400 nanometers.

Figure 2B:
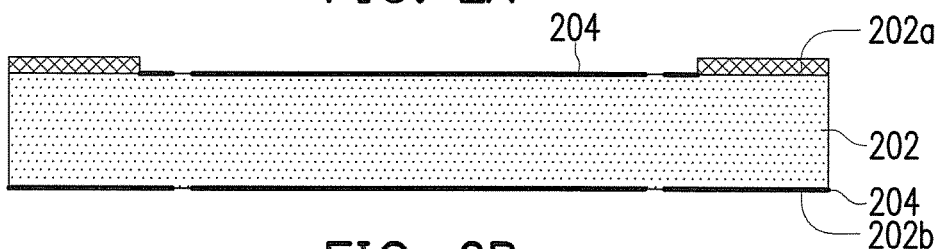

Next, as shown in FIG. 2B, the first surface 202a and the insulating layer 204 of the second surface 202b are patterned, thereby defining the locations of the subsequently formed first weakening structure 250, the second weakening structure 260 and the observation windows 219 and 229.

Figure 2C:
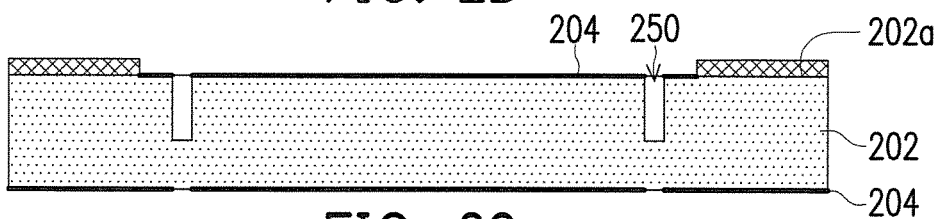

Then, as shown in FIG. 2C, the semiconductor substrate 202 is etched using the insulating layer 204 of the first surface 202a, or a coated photoresist having a defined pattern, as a mask to form the first weakening structure 250. In the etching step here, for example, the first weakening structure 250 having a high aspect ratio is formed by plasma etching and such dry etching technique. Of course, in other embodiments, the etching step here may be replaced by the stealth laser cutting technique of U.S. Pat. No. 6,992,026 or partial ion implantation and heat treatment and such related modification method. The details will be described in the description below. Here, a depth of the first weakening structure 250 is approximately 150 microns. So far, aside from the second weakening structure 260 and the observation window 219, the substrate structure having a prototype substrate 210 is roughly complete.

Since the substrates 210 and 220 of the sample collective device 200 of the present embodiment have similar structures, the steps of FIGS. 2A-2C may be repeated to manufacture another substrate structure having the prototype substrate 220.

Figure 2D:
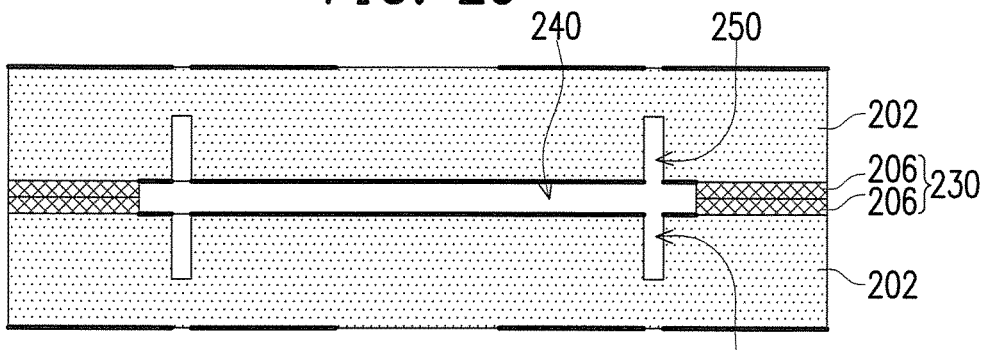

Next, as shown in FIG. 2D, the bonding layers 206 of the two substrate structures formed in FIG. 2C are connected together, for example, by anodic bonding or fusion bonding, wherein the two bonding layers 206 act as the spacer 230 after bonding, and the sample containing space 240 is formed between the two semiconductor substrates 202 of the substrate structure.

Figure 2E:
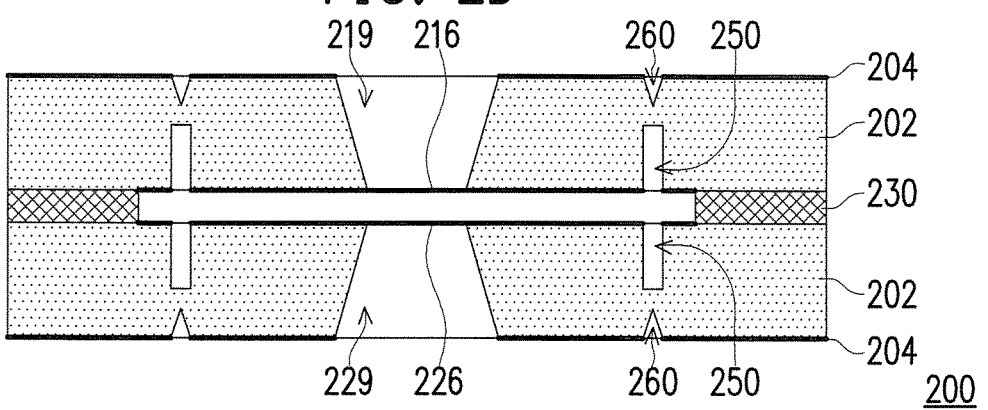

Then, as shown in FIG. 2E, the second weakening structure 260 and the observation windows 219 and 229 are formed by using the insulating layer 204 on the outside of the two substrate structures as a mask, and for example, removing a part of the semiconductor substrate 202 using a wet etching technique. More specifically, for example, non-isotropic etching is performed on the semiconductor substrate 202 to the first thin film 216 using potassium hydroxide etching liquid to further obtain the second weakening structure 260 and the observation windows 219 and 229. The depth of the etching in the non-isotropic etching may be controlled by a design width of the etching opening. Therefore, the depth of the second weakening structure 260 may be determined by the width of the opening of the insulating layer 204 which is acting as a mask. Along the same reasoning, by designing the insulating layer 204 to correspond to the width of the opening of the observation windows 219 and 229, then the observation windows 219 and 229 may be formed such that a part of the insulating layer 204 located at the opposite side of the semiconductor substrate 202 is exposed and acts as the aforementioned thin films 216 and 226.

Of course, the aforementioned manufacturing process is only an example of a possible manufacturing method of the sample collective device 200. In actuality, after referencing the aforementioned embodiments, a person skilled in the art may modify, replace or adjust the steps of the manufacturing process according to the technology standards at the time of applicability. For example, as the semiconductor etching manufacturing process, for example: dry etching or wet etching techniques; or, as mechanical method, for example: cutting wheel or grinding removal method. Or, the partial regions inside the semiconductor substrate 202 may be weakened suitably by the stealth laser cutting technique developed in U.S. Pat. No. 6,992,026.

Up until here, the manufacturing of the sample collective device 200 is roughly completed.

Referring to FIG. 1B again, because the first weakening structure 250 and the second weakening structure 260 of the present embodiment are located outside of the region of the spacer 230, when the first weakening structure 250 and the second weakening structure 260 receive an external force and is broken, the different parts of the substrates 210 and 220 which are located at the two sides of the first weakening structure 250 and the second weakening structure 260 may separate from each other such that the sample containing space 240 is opened. In addition, in order to separate the different parts of the substrates 210 and 220 effectively, a first distance L1 between the bottom of the first weakening structure 250 and the bottom of the second weakening structure 260 may be designed. For example, the first distance L1 may be made smaller than or equal to ⅔ of the thickness of the substrate 210 or 220. For example, if the thickness of the substrate 210 or 220 is 400 microns, then the first distance L1 is designed to 100 microns.

Figure 3A:
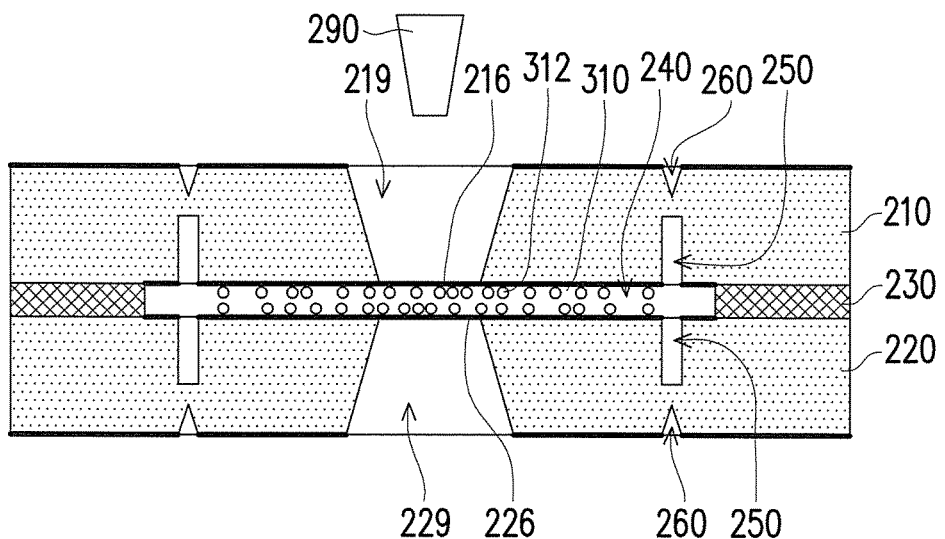
FIGS. 3A-3C illustrate a preparation process of a dry sample specimen according to an embodiment of the present disclosure sequentially.
Figure 3B:
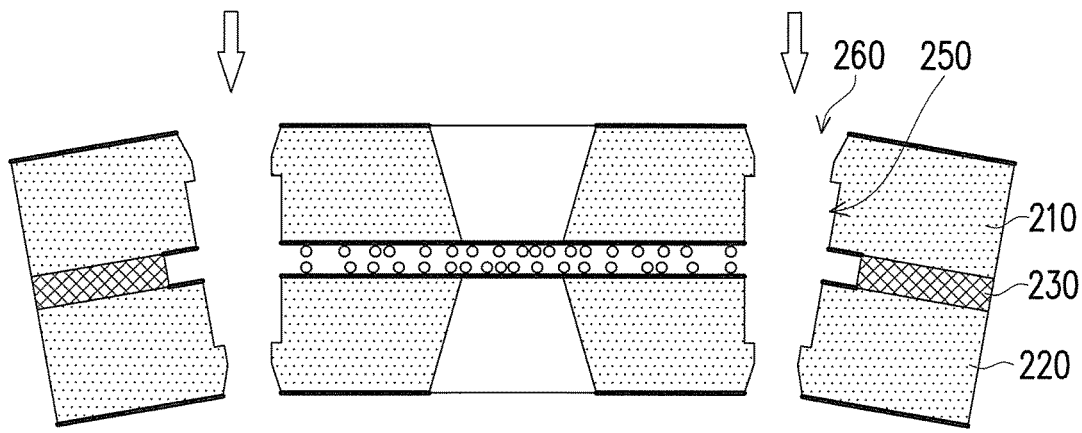
Figure 3C:
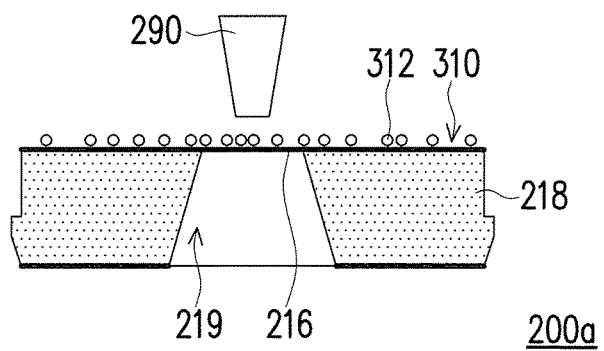

A method for preparing a dried sample specimen using the sample collective device 200 is further described below. FIGS. 3A-3C illustrate a preparation process of a dried sample specimen according to an embodiment of the present disclosure sequentially.

First, as shown in FIG. 3A, a liquid sample 310 is loaded into the sample collective device 200 or the sample containing space 240 of a possible modified configuration of the sample collective device 200, wherein the liquid sample 310 containing the suspended particles 312 are absorbed into the sample containing space 240 through the capillary phenomenon generated by the substrates 210 and 220 and the spacer 230. In addition, in the present embodiment, the process of loading the liquid sample 310 may be assisted by suction attraction or pressurized injection and such methods such that the liquid sample 310 may enter the sample containing space 240 smoothly.

Furthermore, the liquid sample 310 is dried such that the suspended particles 312 adhere onto the thin films 216 and 228, wherein a method of drying may be by natural transpiration, vacuum drying, low humidity drying environment, heat drying, low temperature drying, nitrogen drying environment or inert gas drying environment. A purpose of drying is to remove composition having a higher vapor pressure (moisture, for example) in the liquid sample 310 and make the remaining components in the liquid sample 310 (suspended particles 312, for example) adhere to the surfaces of the thin films 216 and 226 and not have mobility, such that the separation of the two substrates 210 and 220 may be performed subsequently. The vapor pressure here refers to the saturated vapor pressure under a particular temperature (room temperature, for example). Of course, the dried liquid sample 310 may also keep a part of its liquid composition or characteristic, for example, the lower vapor pressure macromolecule composition, or, the moisture and such which are absorbed, interlocked or cladded in the residual particulate matter.

In the present embodiment, because the substrates 210 and 220 have corresponding observation windows 219 and 229 respectively, and the observation windows 219 and 229 penetrate the bottoms 218 and 228 respectively, the corresponding thin films 216 and 226 are exposed. Therefore, in this step, the liquid sample 310 in the sample containing space 240 may be pre-observed by a transmission electron microscope 290.

Next, as shown in FIG. 3B, the different parts of the substrates 210 and 220 located at two sides of the first weakening structure 250 and the second weakening structure 260 may be separated from each other by an external force breaking the first weakening structure 250 and the second weakening structure 260. The first weakening structure 250 and the second weakening structure 260 correspond to a location outside the spacer 230, therefore after parts of the two sides of the sample collective device 200 are removed together with the spacer 230, a central portion of the two substrates 210 and 220 which are remaining may be separated from each other, such that the spacer 230 does not remain on the central portion of the two substrates 210 and 220.

In this way, after the step of separating the substrates 210 and 220 shown FIG. 3B, a bare dried sample specimen 200a as shown in FIG. 3C may be formed. Using the dried sample specimen 200a formed on the substrate 210 as an example, the dried sample specimen 200a includes the thin film 216, the bottom 218, the observation window 219 and a dried liquid sample 310 that is located on the thin film 216. The dried liquid sample 310 includes the suspended particles 312 which are adhered to the surface of the thin film 216. Because the thickness of the liquid sample 310 is limited by the height of the sample containing space 240, it is not easy for the suspended particles 312 to move during the drying process, therefore the aggregation phenomenon may be prevented during the drying process such that the distribution state of the suspended particles 312 in the liquid sample 310 may be maintained.

In addition, because an overall thickness of the bare dried sample specimen 200a is extremely small and the observation window 219 is formed on the dried sample specimen 200a, the dried sample specimen 200a may not only be applicable to, for example, the optical microscope, the scanning electron microscope and such observation microscopes having lower thickness limit for the sample specimen, but also as shown in FIG. 3C, the dried sample specimen 200a may be placed under the transmission electron microscope 290 such that the electron beam penetrates the dried sample specimen 200a and the dried sample specimen 200a may be observed by the transmission electron microscope 290.

In this way, in the preparation process shown in FIGS. 3A-3C, a user may perform observations on the liquid sample 310 through the same sample collective device 200 before being dried, wherein a method for observation, for example, may be through the description disclosed in Taiwan patent number 1330380; the sample collective device 200 may also be opened after drying, such that observations may be performed on the uniform bare dried sample specimen 200a.

Although the aforementioned embodiments disclose structurally the same substrates 210 and 220 to form the dried sample specimen 200a through the preparation process shown in FIGS. 3A-3C, however the present disclosure is not limited thereto.

Figure 4A:
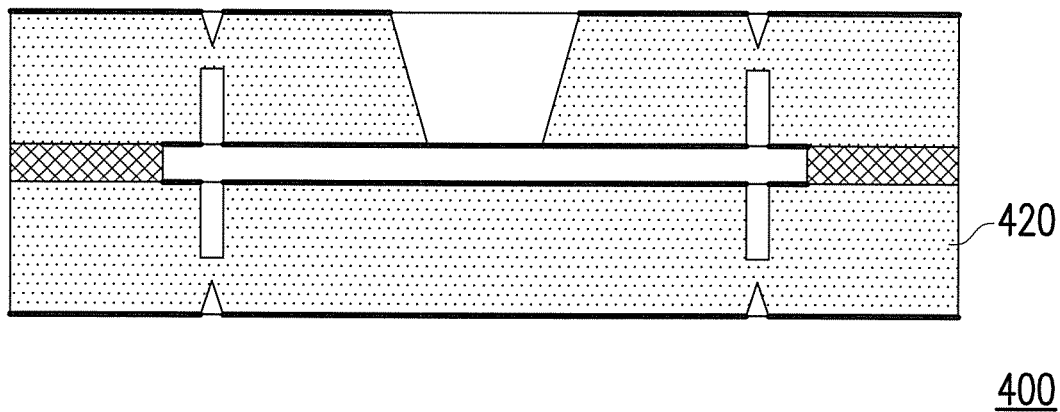
FIG. 4A illustrates a sample collection device according to another embodiment of the present disclosure.

FIG. 4A illustrates a sample collection device 400 according to another embodiment of the present disclosure. The sample collective device 400 of the present embodiment is roughly similar to the sample collective device 200 of the aforementioned embodiment. Therefore, the same or already understood technical content will not be repeated here. A difference between the sample collective device 400 and the sample collective device 200 of the aforementioned embodiment includes: a substrate 420 of the present embodiment does not have an observation window. In other words, in the patterning step shown in FIG. 2B, it is opted to not define the opening corresponding to the observation window on the insulating layer 204 of the second surface 202b.

Figure 4B:
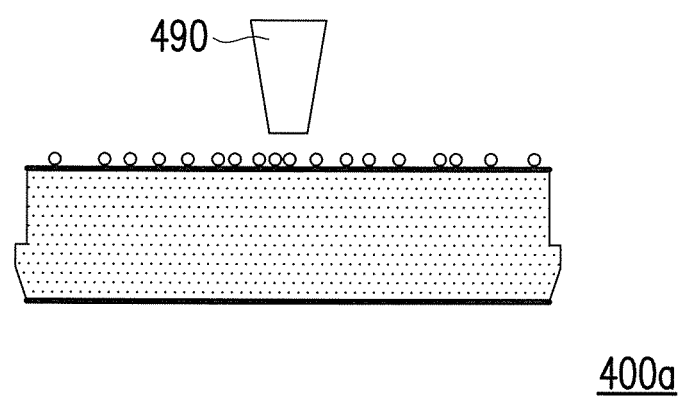
FIG. 4B illustrates a dried liquid sample specimen prepared by the sample collection device of FIG. 4A.

In this way, after the preparation process shown in FIGS. 3A-3C, the substrate 420 may form into the dried sample specimen 400a as shown in FIG. 4B. The difference between the dried sample specimen 400a of the present embodiment and the dried sample specimen 200a of the aforementioned embodiment lies in not having the observation window. Therefore, the dried sample specimen 400a may be applicable to the optical microscope, the scanning electron microscope and such observation microscopes having lower thickness limit for the sample specimen, but also may be observed directly using the atomic force microscope 490.

The aforementioned embodiments of the present disclosure provide a separated bare dried sample specimen, such as the dried sample specimen 200a and the dried sample specimen 400a. Compared to a conventional shielded sample specimen, the dried sample specimen of the present disclosure may further decrease a problem of absorption and scattering, and assists in increasing the accuracy of the microscope observation.

Figure 5:
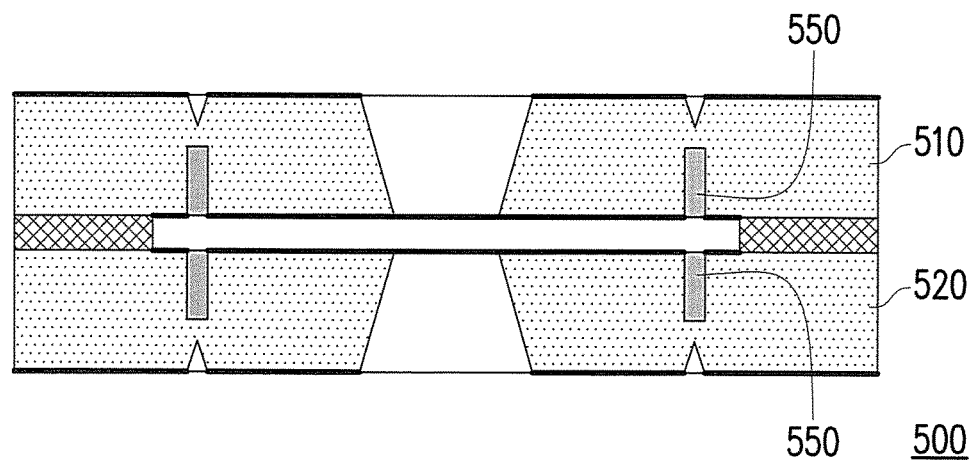
FIGS. 5-7 illustrate various sample collection devices according to other embodiments of the present disclosure.
Figure 6:
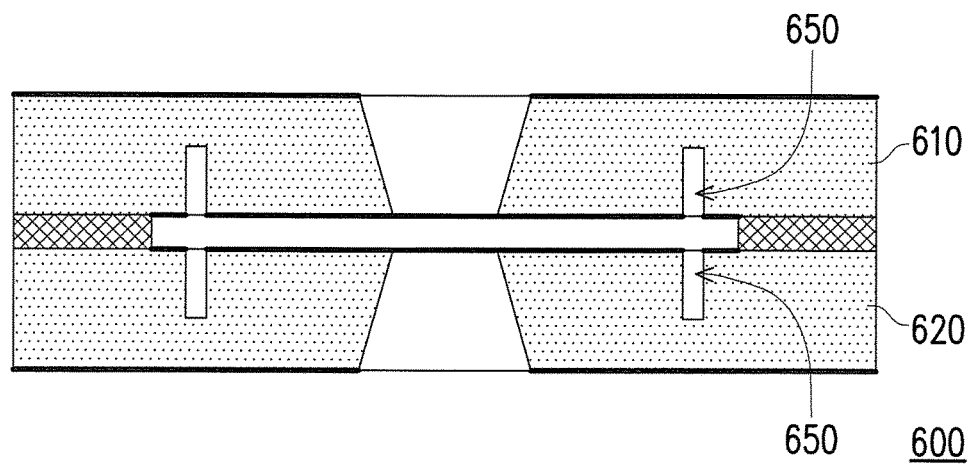
Figure 7:
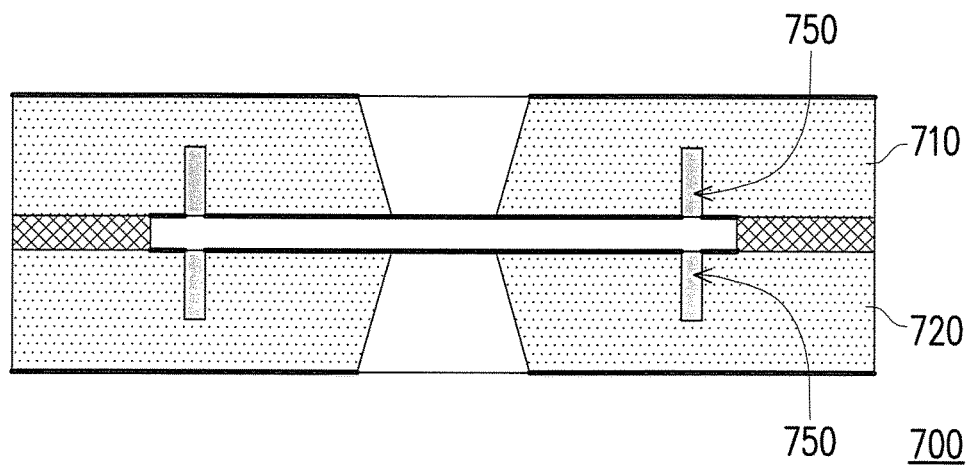

Other types of the sample collective device of the present disclosure which may be available are described with examples below. FIGS. 5-7 illustrate various sample collection devices according to other embodiments of the present disclosure.

A sample collective device 500 shown in FIG. 5 is roughly similar to the sample collective device 200 of the aforementioned embodiment. Therefore, the same or already understood technical content will not be repeated here. A difference between the sample collective device 500 and the sample collective device 200 of the aforementioned embodiment includes: a first weakening structure 550 of the present embodiment, for example, is a modified material formed by modifying a part of a substrates 510 and 520. More specifically, the step of etching the semiconductor substrate 202 as shown in FIG. 2C may be replaced by the stealth laser cutting technique of U.S. Pat. No. 6,992,026 or partial ion implantation and heat treatment and such related modification method, to modify a part of the semiconductor substrate 202 to form the material shown in the present embodiment, for example, the first weakening structure 550 of polycide and having a high density lattice dislocation structure.

A sample collective device 600 shown in FIG. 6 is roughly similar to the sample collective device 200 of the aforementioned embodiment. Therefore, the same or already understood technical content will not be repeated here. A difference between the sample collective device 600 and the sample collective device 200 of the aforementioned embodiment includes: an outer side of substrates 610 and 620 of the sample collective device 600 of the present embodiment do not have a second weakening structure. In other words, under the premise that a separation of the substrates 610 and 620 may be implemented, the present disclosure could only select to form the first weakening structure 650 at the inner side of the substrates 610 and 620, and omit the second weakening structures at the outer side. The first weakening structure 650 of the present embodiment, for example, is a strip shaped depressions, as shown in FIG. 1A.

A sample collective device 700 shown in FIG. 7 is roughly similar to the sample collective device 500 of the aforementioned embodiment. Therefore, the same or already understood technical content will not be repeated here. A difference between the sample collective device 700 and the sample collective device 500 of the aforementioned embodiment includes: an outer side of the substrates 710 and 720 of the sample collective device 700 of the present embodiment do not have a second weakening structure. In other words, under the premise that a separation of the substrates 710 and 720 may be implemented, the present disclosure could only select to form the first weakening structure 750 at the inner side of the substrates 710 and 720, and omit the second weakening structures at the outer side. The first weakening structure 750 of the present embodiment, for example, is a modified material formed by modifying a part of the substrates 710 and 720.

FIGS. 8-11 illustrate various sample collection devices according to other embodiments of the present disclosure. Sample collective devices 800, 900, 1000, 1100 illustrated in FIGS. 8-11 are roughly similar to the sample collective devices 200, 500, 600, 700 of the aforementioned embodiment respectively. Therefore, the same or already understood technical content will not be repeated here. A difference between the sample collective devices 800, 900, 1000, 1100 and the sample collective devices 200, 500, 600, 700 of the aforementioned embodiments respectively includes: in the sample collective devices 800, 900, 1000, 1100 illustrated in FIGS. 8-11, a cavity is formed at a surface of the inner side of the substrate corresponding to the sample containing space 240, such that the amount of liquid sample that may be accommodated by the sample containing space may be adjusted. The first weakening structure formed, for example, is located outside the cavity.

Figure 8:
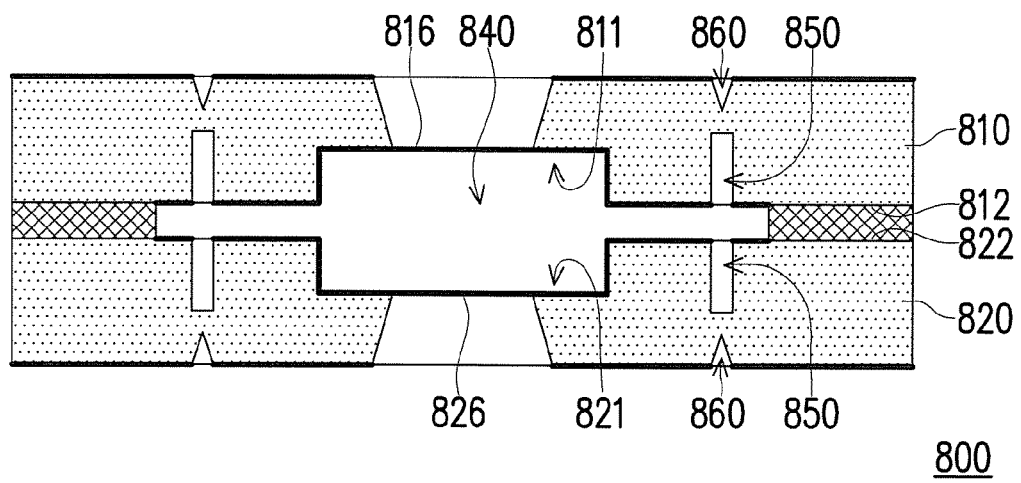
FIGS. 8-11 illustrate various sample collection devices according to other embodiments of the present disclosure.

More specifically, in the sample collective device 800 of FIG. 8, cavities 811 and 821 are formed at the first surfaces 812 and 822 of the substrates 810 and 820 respectively. The cavities 811 and 821 are located within the sample containing space 840, and the first weakening structure 850 and the second weakening structure 860 are located outside the cavities 811 and 821. Regarding the manufacturing process, for example, a cavity is formed by first etching the first surface 202a of the semiconductor substrate 202 as shown in FIG. 2A, and then chemical vapor deposition is subsequently performed to form the insulating layer 204 with a thickness of approximately 100 nanometers. In this way, the insulating layer 204 covers the bottom of the cavity, and the thin films 816 and 826 as shown in FIG. 8 are formed in the subsequent manufacturing process.

Figure 9:
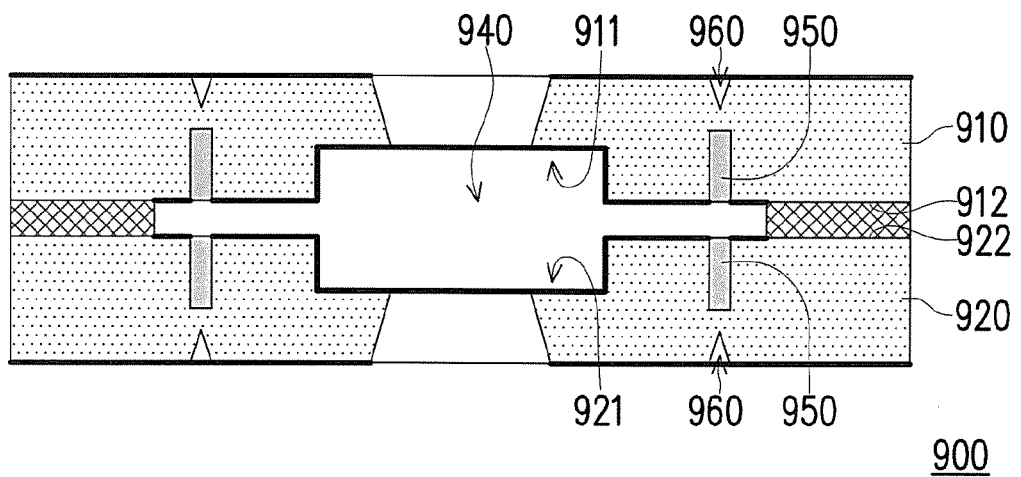

Similarly, in the sample collective device 900 of FIG. 9, cavities 911 and 921 are formed at the first surfaces 912 and 922 of the substrates 910 and 920 respectively. The cavities 911 and 921 are located within the sample containing space 940, and the first weakening structure 950 and the second weakening structure 960 are located outside the cavities 911 and 921. The manufacturing method of the cavities 911 and 921 are similar to the aforementioned cavities 811 and 821 and will not be repeated here. In addition, the first weakening structure 950 of FIG. 9 is similar to the first weakening structure 550 of FIG. 5 and is a modified material formed by modifying a part of the substrates 910 and 920.

Figure 10:
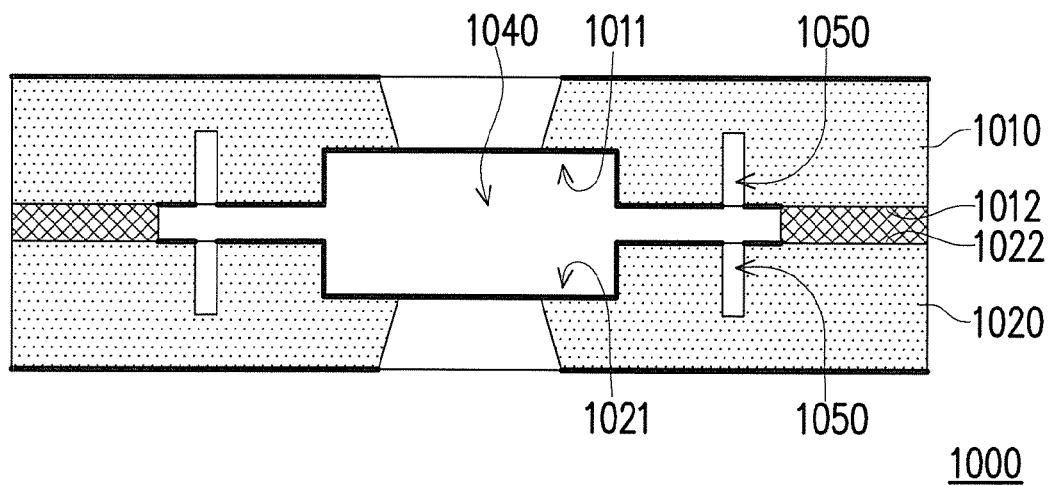

In the sample collective device 1000 of FIG. 10, cavities 1011 and 1021 are formed at the first surfaces 1012 and 1022 of the substrates 1010 and 1020 respectively. The cavities 1011 and 1021 are located within the sample containing space 1040, and the first weakening structure 1050 and the second weakening structure 1060 are located outside the cavities 1011 and 1021. The manufacturing method of the cavities 1011 and 1021 are similar to the aforementioned cavities 811 and 821 and will not be repeated here. In addition, the sample collective device 1000 of FIG. 10 is similar to the sample collective device 600 of FIG. 6 and an outer side of substrates 1010 and 1020 do not have a second weakening structure.

Figure 11:
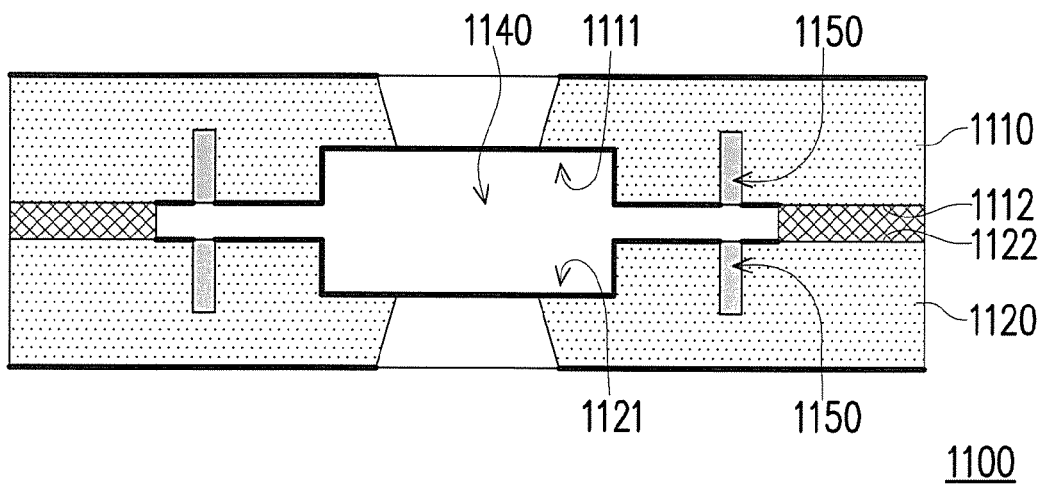

Similarly, in the sample collective device 1100 of FIG. 11, cavities 1111 and 1121 are formed at the first surfaces 1112 and 1122 of the substrates 1110 and 1120 respectively. The cavities 1111 and 1121 are located within the sample containing space 1140, and the first weakening structure 1150 is located outside the cavities 1111 and 1121. The manufacturing method of the cavities 1111 and 1121 are similar to the aforementioned cavities 811 and 821 and will not be repeated here. In addition, the first weakening structure 1150 of FIG. 11 is similar to the first weakening structure 750 of FIG. 7 and is a modified material formed by modifying a part of the substrates 1110 and 1120.

It should be noted, the aforementioned embodiments only describe a number of possible configurations of the sample collective device of the present disclosure. It will be apparent to those skilled in the art that various modifications and variations can be made to the structure of the present disclosure without departing from the scope or spirit of the present disclosure. For example, the observation window could be formed only on a single substrate of the sample collective devices 500-1100 of FIGS. 5-11. Or, the cavity could only be formed on a single substrate of the sample collective devices 500-1100 of FIGS. 5-11.

The sample collective device proposed by the present disclosure may be integrated in the wafer level manufacturing process and combine conventional semiconductor manufacturing methods and/or microelectro mechanical system manufacturing process to implement the make and increase manufacturing efficiency.

Figure 12A:
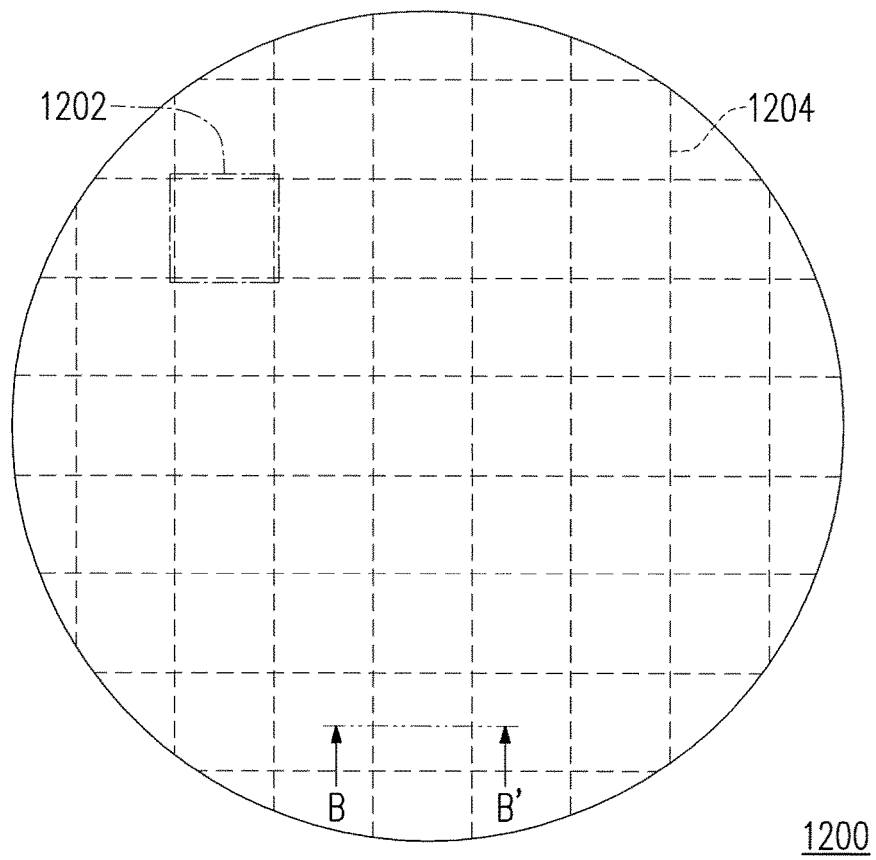
FIG. 12A illustrates a sample collection device array according to an embodiment of the present disclosure.
Figure 12B:
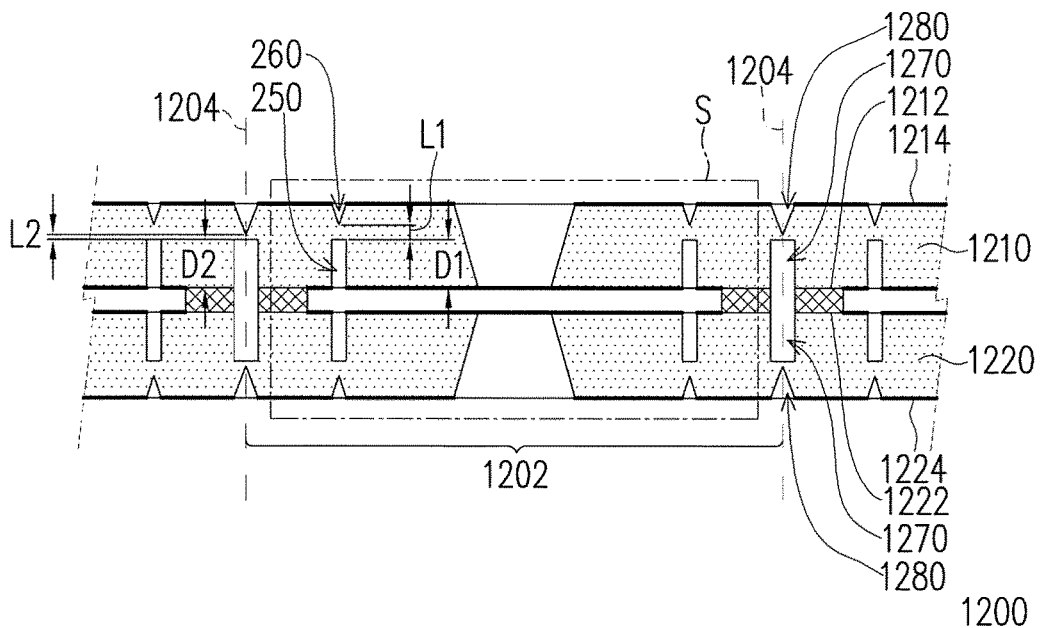
FIG. 12B is a cross-sectional diagram of the sample collection device of FIG. 12A along the line B-B'.

FIG. 12A illustrates a sample collection device array according to an embodiment of the present disclosure. FIG. 12B is a cross-sectional diagram of the sample collection device 1200 of FIG. 12A along the line B-B'. The sample collection device 1200 of the present embodiment, for example, is formed by performing the manufacturing processes shown in FIGS. 2A-2E to a silicon wafer or other base material. The related manufacturing steps are similar and will not be repeated here.

As shown in FIGS. 12A and 12B, the sample collective device array 1200 formed includes a plurality of sample collective device 1202, for example, which are the sample collective devices 200, 400, 500, 600, 700, 800, 900, 1000, 1100 of the aforementioned embodiments or other possible variations. After the manufacturing of a plurality of the sample collective devices 1202 is complete, the sample collective devices 1202 are arranged in an array and connected together and defined by a plurality of cutting paths 1204 on the sample collective device array 1200. In other words, after sample collective device array 1200 is cut along the cutting paths 1204, a plurality of sample collective devices 1202 separated from each other may be obtained.

Regarding the content wherein a plurality of sample collective devices 200, 400, 500, 600, 700, 800, 900, 1000 or 1100 may be used as the sample collective device 1202, it will not be repeated here. As shown in FIG. 12B, a structure in a region surrounded by the dashed line box S may be replaced by the sample collective devices 200, 400, 500, 600, 700, 800, 900, 1000 or 1100 shown in FIG. 1B, 4A, 5, 6, 7, 8, 9, 10 or 11.

In the present embodiment, the sample collective devices 1202 may be separated along the cutting path 1204 by laser cutting, cutting wheel cutting or grinding removal or such method. In addition, it is selected in the present embodiment to form the first weakening structure at a position of the cutting path 1204 to assist the separation step along the cutting path.

In the present embodiment, a third weakening structure 1270 is formed at the first surface 1212 of the substrate 1210 and the first surface 1222 of the substrate 1220 respectively, and a corresponding fourth weakening structure 1280 is formed at the second surface 1214 of the substrate 1210 and the second surface 1224 of the substrate 1220 respectively. The third weakening structure 1270 and the fourth weakening structure 1280 referred to here are structures with structural strengths lower than other parts of the substrates 1210 and 1220. In actuality, similar to the first weakening structure and the second weakening structure of the aforementioned embodiment, the depressions may be formed by removing a part of the substrates 1210 and 1220, or implemented by performing modifications to partial regions of the substrates 1210 and 1220.

The third weakening structure 1270 and the fourth weakening structure 1280 are located on the cutting path 1204, and a possible configuration of the cutting path 1204, for example, is a structure having grids with a same distribution, or a plurality of block structures distributed on the cutting path 1204.

Figure 13:
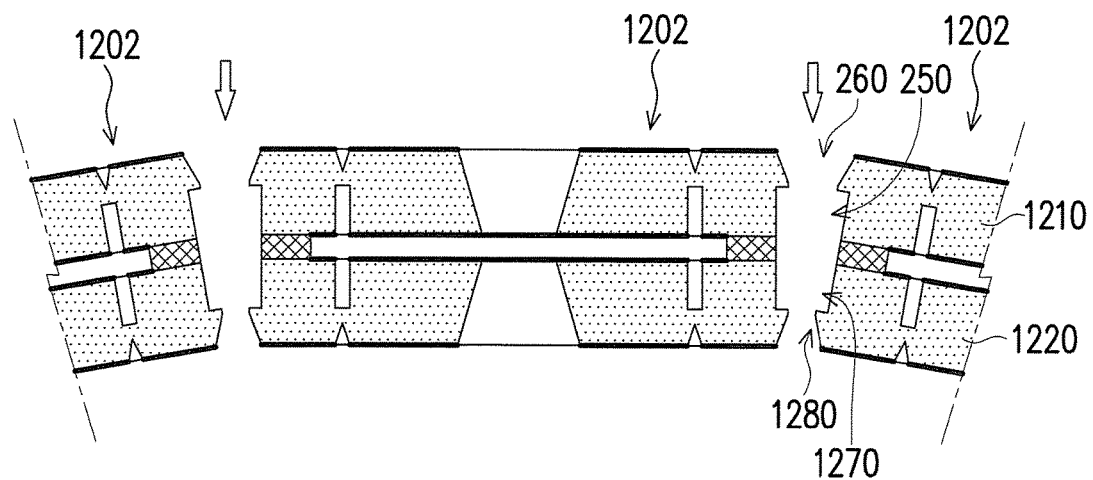
FIG. 13 is schematic diagram performing singulation of the sample collection device array of FIGS. 12A and 12B.

FIG. 13 is schematic diagram performing singulation of the sample collection device array of FIGS. 12A and 12B. Because the third weakening structure 1270 and the fourth weakening structure 1280 are formed on the cutting path 1204 of the present embodiment, when the third weakening structure 1270 and the fourth weakening structure 1280 receive an external force and is broken, then the different parts of the substrates 1210 and 1220 located at the two sides of the third weakening structure 1270 and the fourth weakening structure 1280 may be separated from each other. In other words, two adjacent substrates 1210 and 1220 of the sample collective device 1202 are separated from each other by this action. As a possible situation, laser cutting, cutting wheel cutting or grinding removal and such method to cut the sample collective device array 1200 may not be necessary and a force may be applied directly to the sample collective device array 1200 manually or by an auxiliary tool to facilitate the separation of the plurality of sample collective devices 1202.

In addition, as shown in FIG. 12B, in order to separate the two adjacent sample collective devices 1202 effectively, a design may be implemented on a second distance L2 between a bottom of the third weakening structure 1270 and a bottom of the fourth weakening structure 1280. For example, the second distance L2 may be made smaller than or equal to half of the thickness of the substrate. For example, if the thickness of the substrate 1210 or 1220 is 400 microns, then the second distance L2 may be designed to 50 microns. In addition, compared to the distance L1 between the bottom of the first weakening structure 250 and the bottom of the second weakening structure 260, the second distance L2 may be designed smaller than the first distance L1. In this way, the substrates 1210 and 1220 breaking along the bottom of the first weakening structure 1250 and the second weakening structure 1250 may be prevented when the two adjacent sample collective devices 1202 are separated along the cutting path.

In other words, by the aforementioned design, the separation of the sample collective device array 1200 into a plurality of sample collective devices 1202 is completed even under conditions without using any laser or mechanical cutting machinery, and the sample collective devices 1202 is prepared to the dried sample specimen 200a as shown in FIG. 3C. More specifically, after manufacturing of the sample collective device array 1200 is completed; firstly, the external force is applied to the third weakening structure 1270 and the fourth weakening structure 1280 along the cutting path 1204 to separate out the plurality of sample collective devices 1202. Then, the steps shown in FIGS. 3A-3C are performed, filling the liquid sample 310, drying the liquid sample 310, and applying an external force again to break the first weakening structure 250 and the second weakening structure 260 to form the dried sample specimen 200a as shown in FIG. 3C.

In the present embodiment, the third weakening structure 1270 and the first weakening structure 250, for example, are formed in the same step shown in FIG. 2C. More specifically, in addition to patterning the insulating layer 204 of the first surface 202a as shown in FIG. 2B, the bonding layer 206 is patterned by a similar etching technique to define the location of the third weakening structure 1270. In this way, in the subsequent step of etching the semiconductor substrate 202 as shown in FIG. 2C, the first weakening structure 250 and the third weakening structure 1270 may be formed at the same time. At this time, if plasma etching and such dry etching technique is adopted to form the first weakening structure 250 and the third weakening structure 1270, then as shown in FIG. 12B, a depth D1 of the first weakening structure 250 formed is substantially equal to a depth D2 of the third weakening structure 1270 that is formed.

Figure 14:
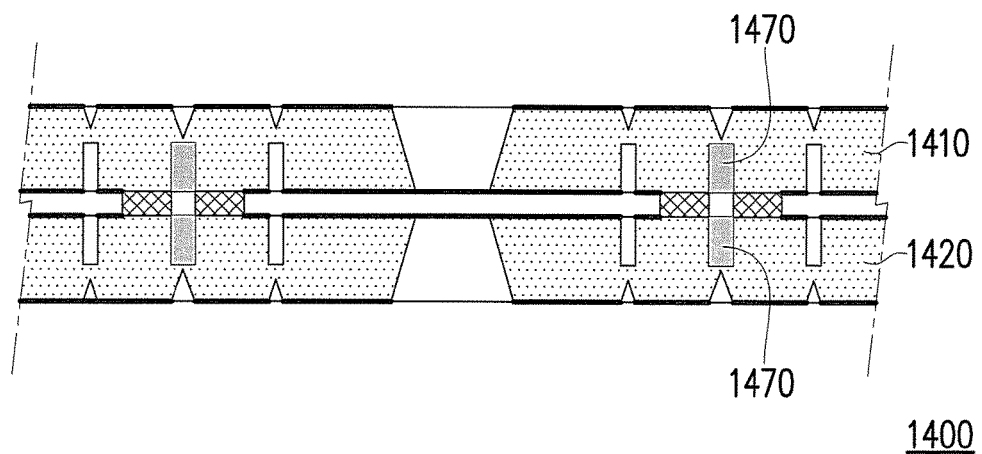
FIGS. 14-16 illustrate various sample collection device arrays according to other embodiments of the present disclosure.
Figure 15:
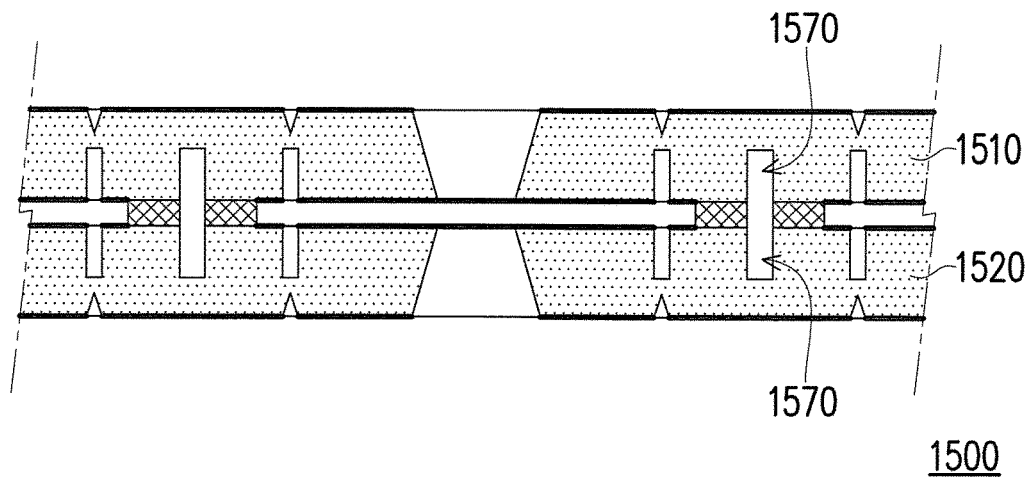
Figure 16:
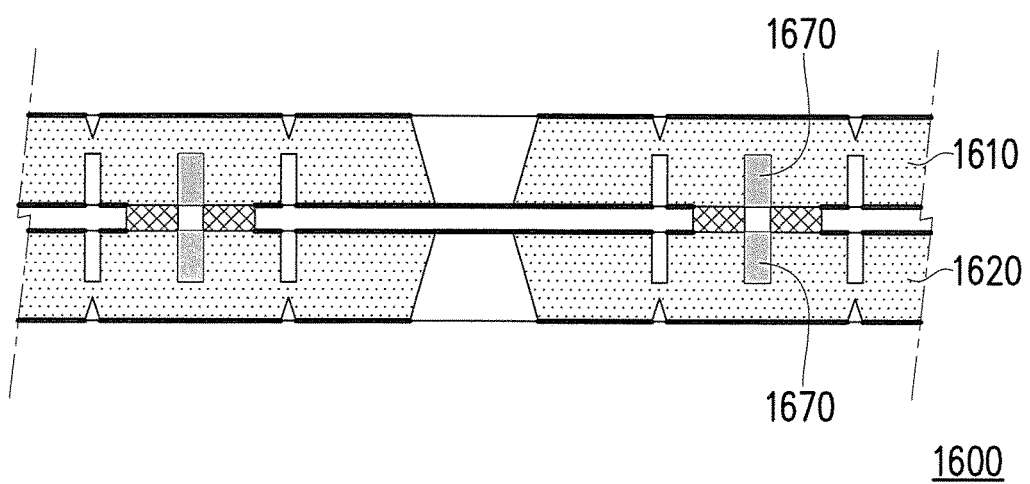

Some possible variations of the third weakening structure and the fourth weakening structure are described below. FIGS. 14-16 illustrate various sample collection device arrays according to other embodiments of the present disclosure.

A sample collective device array 1400 shown in FIG. 14 is roughly similar to the sample collective device array 1200 of the aforementioned embodiment. Therefore, the same or already understood technical content will not be repeated here. A difference between the sample collective device array 1400 and the sample collective device array 1200 of the aforementioned embodiment includes: a third weakening structure 1410 of the present embodiment, for example, is a modified material formed by modifying a part of a substrates 1410 and 1420. More specifically, the etching step may be replaced by the stealth laser cutting technique of U.S. Pat. No. 6,992,026 or partial ion implantation and heat treatment and such modification method, to modify a part of the substrates 1410 and 1420 to form the material shown in the present embodiment, for example, the third weakening structure 1470 of polycide and having a high density lattice dislocation structure.

A sample collective device array 1500 shown in FIG. 15 is roughly similar to the sample collective device array 1200 of the aforementioned embodiment. Therefore, the same or already understood technical content will not be repeated here. A difference between the sample collective device array 1500 and the sample collective device array 1200 of the aforementioned embodiment includes: an outer side of substrates 1510 and 1520 of the sample collective device array 1500 of the present embodiment do not have a fourth weakening structure. In other words, under the premise that a separation of the substrates 1510 and 1520 may be implemented, the present disclosure could select only to form the third weakening structure 1570 at the inner side of the substrates 1510 and 1520, and omit the fourth weakening structures at the outer side.

A sample collective device array 1600 shown in FIG. 16 is roughly similar to the sample collective device array 1400 of the aforementioned embodiment. Therefore, the same or already understood technical content will not be repeated here. A difference between the sample collective device array 1600 and the sample collective device array 1400 of the aforementioned embodiment includes: an outer side of substrates 1610 and 1620 of the sample collective device array 1600 of the present embodiment do not have a fourth weakening structure. In other words, under the premise that a separation of the substrates 1610 and 1620 may be implemented, the present disclosure could select only to form the third weakening structure 1670 at the inner side of the substrates 1610 and 1620, and omit the fourth weakening structures at the outer side.

It will be apparent to those skilled in the art that various modifications and variations can be made to the structure of the present disclosure without departing from the scope or spirit of the present disclosure. In view of the foregoing, it is intended that the present disclosure cover modifications and variations of the present disclosure provided they fall within the scope of the following claims and their equivalents.

What is claimed is:

1. A sample collective device, comprising:
two substrates, wherein each of the two substrates has a first surface and a second surface, and the two first surfaces are disposed facing each other; and
a spacer, disposed between the two first surfaces for bonding and fixing the two substrates to form a sample containing space between the two substrates, wherein each of the two substrates has a first weakening structure, the first weakening structure is located at a periphery of the sample containing space and exposed on the first surface, and the first weakening structure is adapted to separate the two substrates in response to an external force.

2. The sample collective device as claimed in claim 1, wherein the first weakening structure comprises a depression on the first surface.

3. The sample collective device as claimed in claim 1, wherein the first weakening structure comprises a modified material formed by modifying a part of the substrate.

4. The sample collective device as claimed in claim 1, wherein the first weakening structure comprises two corresponding strip shaped structures or a plurality of block shaped structures distributed on two corresponding strip shaped paths.

5. The sample collective device as claimed in claim 1, wherein each of the substrates further comprises a second weakening structure, the second weakening structure is exposed on the second surface, and the first weakening structure and the second weakening structure are aligned with each other in a thickness direction of the substrates.

6. The sample collective device as claimed in claim 5, wherein the second weakening structure comprises a depression on the second surface.

7. The sample collective device as claimed in claim 5, wherein the second weakening structure comprises two corresponding strip shaped structures or a plurality of block shaped structures distributed on two corresponding strip shaped paths.

8. The sample collective device as claimed in claim 5, wherein a bottom of the first weakening structure and a bottom of the second weakening structure are apart by a first distance, and the first distance is smaller than or equal to two thirds of a thickness of each of the substrates.

9. The sample collective device as claimed in claim 1, wherein each of the substrates further comprises a cavity, the cavity is located at the first surface and is located within the sample containing space, and the first weakening structure is located outside the cavity.

10. The sample collective device as claimed in claim 1, wherein each of the substrates further comprises an observation window, the observation window is located at the second surface and corresponding to the sample containing space.

11. A sample collective device array, comprising a plurality of the sample collective devices as claimed in claim 1, wherein the sample collective devices are arranged in an array and connected together, and are defined by a plurality of cutting paths.

12. The sample collective device array as claimed in claim 11, wherein each of the substrates further comprises a third weakening structure, the third weakening structure is located on the cutting path and is exposed on the first surface.

13. The sample collective device array as claimed in claim 12, wherein the third weakening structure comprises a depression on the first surface.

14. The sample collective device array as claimed in claim 12, wherein the third weakening structure comprises a modified material formed by modifying a part of the substrates.

15. The sample collective device array as claimed in claim 12, wherein the third weakening structure comprises a grid shape structure or a plurality of block shaped structures distributed on the cutting path.

16. The sample collective device array as claimed in claim 12, wherein each of the substrates further comprises a fourth weakening structure, the fourth weakening structure is located on the cutting path and is exposed on the second surface.

17. The sample collective device array as claimed in claim 16, wherein the fourth weakening structure comprises a depression on the second surface.

18. The sample collective device array as claimed in claim 16, wherein the fourth weakening structure comprises a grid shape structure or a plurality of block shaped structures distributed on the cutting path.

19. The sample collective device array as claimed in claim 16, wherein a bottom of the third weakening structure and a bottom of the fourth weakening structure are apart by a second distance, and the second distance is smaller than or equal to half of the thickness of each of the substrates.

20. The sample collective device array as claimed in claim 12, wherein a depth of the first weakening structure is substantially equal to a depth of the third weakening structure.

21. A manufacturing method of a sample collective device, comprising:

forming an insulating layer on a first surface and a second surface of a semiconductor substrate, wherein the first surface is opposite to the second surface;

removing the insulating layer located at a periphery of the first surface, and forming a bonding layer on the exposed first surface;

patterning the insulating layer on the first surface and the second surface, wherein the insulating layer on the first surface exposes a part of the first surface, and the insulating layer on the second surface exposes a part of the second surface;

forming a first weakening structure on the part of the first surface exposed by the insulating layer;

repeating the aforementioned steps on another semiconductor substrate; and bonding the two semiconductor substrates together by the bonding layer of each, wherein the two bonding layers form a spacer which is used to connect and fix the two semiconductor substrates, and a sample containing space is formed between the two semiconductor substrates and the spacer.

22. The manufacturing method of the sample collective device as claimed in claim 21, further comprising:

forming a second weakening structure on the part of the second surface of each of the semiconductor substrates exposed by the insulating layer, wherein a location of the second weakening structure corresponds with a location of the first weakening structure.

23. The manufacturing method of the sample collective device as claimed in claim 22, wherein a method for forming the second weakening structure on each of the semiconductor substrates comprises wet etching.

24. The manufacturing method of the sample collective device as claimed in claim 21, further comprising:

forming an observation window on the part of the second surface of each of the semiconductor substrates exposed by the insulation layer, wherein the observation window penetrates the semiconductor substrate and exposes the insulating layer on the first surface.

25. The manufacturing method of the sample collective device as claimed in claim 21, wherein a method for forming the insulating layer on the semiconductor substrate comprises performing chemical vapor deposition.

26. The manufacturing method of the sample collective device as claimed in claim 21, wherein a method for forming the bonding layer on the semiconductor substrate comprises performing deposition or an oxidation manufacturing process.

27. The manufacturing method of the sample collective device as claimed in claim 21, a method for forming the first weakening structure comprises etching the semiconductor substrate by using the insulating layer on the first surface or coating the insulating layer with a photoresist and defining a pattern as a mask.

28. The manufacturing method of the sample collective device as claimed in claim 27, wherein a method for etching the semiconductor substrate comprises dry etching.

29. The manufacturing method of the sample collective device as claimed in claim 21, wherein a method for bonding the two semiconductor substrates comprises anodic bonding or fusion bonding.

30. A sample collective device, comprising:

two substrates, wherein each of the two substrates has a first surface and a second surface, and the two first surfaces are disposed facing each other; and a spacer, disposed between the two first surfaces for bonding and fixing the two substrates to form a sample containing space between the two substrates, wherein each of the two substrates has a first weakening structure, the first weakening structure is located at a periphery of the sample containing space and exposed on the first surface, and the first weakening structure comprises two corresponding strip shaped structures or a plurality of block shaped structures distributed on two corresponding strip shaped paths.

31. A sample collective device, comprising:

two substrates, wherein each of the two substrates has a first surface and a second surface, and the two first surfaces are disposed facing each other; and a spacer, disposed between the two first surfaces for bonding and fixing the two substrates to form a sample containing space between the two substrates, wherein each of the two substrates comprises:
- a first weakening structure, the first weakening structure is located at a periphery of the sample containing space and exposed on the first surface; and
- a second weakening structure, the second weakening structure is exposed on the second surface, and the first weakening structure and the second weakening structure are aligned with each other in a thickness direction of the substrates.

* * * * *

UNITED STATES PATENT AND TRADEMARK OFFICE
CERTIFICATE OF CORRECTION

| | | |
|---|---|---|
| PATENT NO. | : 9,778,151 B2 | Page 1 of 1 |
| APPLICATION NO. | : 15/073667 | |
| DATED | : October 3, 2017 | |
| INVENTOR(S) | : Pin Chang and Hung-Jen Chen | |

It is certified that error appears in the above-identified patent and that said Letters Patent is hereby corrected as shown below:

On the Title Page

(73) should read: BIO MATERIALS ANALYSIS TECHNOLOGY INC., Hsinchu County (TW)

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*